United States Patent [19]

Franco et al.

[11] Patent Number: 5,162,368
[45] Date of Patent: Nov. 10, 1992

[54] BUTALACTIN AND ITS USE AS PHARMACEUTICAL

[75] Inventors: Christopher M. M. Franco; Erra K. Vijayakumar; Sugata Chatterjee; Bimal N. Ganguli; Jürgen Blumbach, all of Bombay, India

[73] Assignee: Hoechst Aktiengesellschaft, Frankfurt am Main, Fed. Rep. of Germany

[21] Appl. No.: 563,188

[22] Filed: Aug. 6, 1990

[30] Foreign Application Priority Data

Aug. 8, 1989 [EP] European Pat. Off. .......... 89114646

[51] Int. Cl.$^5$ ..................... A61K 31/34; C07D 307/33
[52] U.S. Cl. ....................................... 514/473; 549/318
[58] Field of Search ......................... 549/318; 514/473

[56] References Cited

U.S. PATENT DOCUMENTS

| | | | |
|---|---|---|---|
| 4,070,480 | 1/1978 | Aldridge et al. | 514/473 |
| 4,145,437 | 3/1979 | Aldridge et al. | 514/473 |
| 4,188,331 | 2/1980 | Pernet et al. | 549/318 |

OTHER PUBLICATIONS

"A New Inducer of Anthracycline Biosynthesis" from Streptomyces Viridochromogenes, The Journal of Antibiotics, vol. 35, No. 12, pp. 1722–1723.

Primary Examiner—C. Warren Ivy
Assistant Examiner—Amelia A. Owens
Attorney, Agent, or Firm—Finnegan, Henderson, Farabow, Garrett and Dunner

[57] ABSTRACT

Butalactin, a compound of the formula I

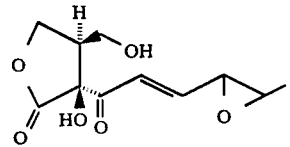

can be produced by cultivation of Streptomyces species Y-86,36923. Butalactin has an antibiotic activity.

3 Claims, 4 Drawing Sheets

BUTALACTIN AND ITS USE AS PHARMACEUTICAL

DESCRIPTION

This invention relates to a compound named Butalactin, a process for its production by cultivating species culture number HIL Y-86,36923 (Str. sp. Y-86,36923) or its mutants or variants as well as the use of Butalactin as a pharmaceutical and a biosynthetic regulator.

Str. sp. Y-86,36923 was isolated from soil collected at Pune, Maharashtra, India and it has been deposited with the Deutsche Sammlung von Mikroorganismen under the conditions of the treaty of Budapest on May 25, 1989 (DSM 5372). Variants and mutants of Str. sp. Y-86,36923 can be obtained in a known manner using a mutagen, such as N-methyl-N-nitro-N'-nitrosoguanidine or ultraviolet light. The microorganism Str. sp. Y-86,36923 belongs to the order Actinomycetales, family Streptomycetaceae and genus Streptomyces.

Str. sp. Y-86,36923 is considered to be a new strain since it differs from the known strains in some of its morphological, cultural and physiological characteristics as will be clear from the description hereinafter. It is considered to be a new strain also because it produces a new antibiotic compound herein called Butalactin as will be clear from the description hereinafter.

As is apparent in the following detailed description of the invention, Butalactin of this invention is a 2,3-disubstituted butanolide antibiotic, but differs from all known disubstituted butanolide metabolites such as A-factor (Bioorg. Khim. 2, 1142-1147, 1976), anthracycline-inducing factors (J. Antibiotics, 35, 1722-1723, 1982; Biotechnology Lett. 5, 591-596, 1983), Virginiae butanolides (J. Antibiotics, 40, 496-504, 1987) and various racemic analogues (J. Antibiotics, 41, 1828-1837, 1988).

Butalactin is a compound of the formula I

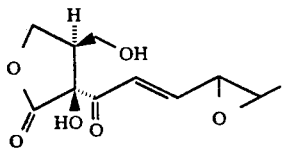

According to IUPAC nomenclature the chemical name of the compound of this invention is 2-(4',5'-epoxy-1'-oxo-2'(E)-hexen)-yl-2-hydroxy-3-hydroxymethyl-2,3-(Z)-butanolide or, alternatively, 2-(4',5'-epoxy-hex-2'(E)-en)oyl-2-hydroxy-4-hydroxymethyl-2,3-(Z)-butanolide.

Chemical Abstract Service (CAS)-Online-Literature Search performed with the search keys of molecular weight and molecular formula also confirmed the fact that Butalactin is a new compound.

The novel antibiotic of this invention is active in vitro against a number of Gram-positive and Gram-negative microorganisms. It is also active in the regulation of biosynthesis of secondary metabolites. Accordingly, it may be used as a therapeutic drug and as a biochemical regulator in the control of antibiotic biosynthesis.

According to the present invention there is also provided a process for the isolation of Str. sp. Y-86,36923 from soil using a nutrient medium at a pH of 6.5 to 8.5 in a known manner.

The nutrient medium used for isolation of the microorganism from soil consists of carbon and nitrogen sources, inorganic nutrient salts and solidifying agents. Sources of carbon may, for example, be glucose, starch, dextrin, glycerol, sucrose or molasses. Sources of nitrogen may, for example, be peptone, yeast extract, beef extract, malt extract, casein or amino acids such as arginine or asparagine. The solidifying agent may, for example, be agar. The inorganic nutrient salts may, for example, be salts of sodium, potassium, magnesium, calcium, phosphorus or sulfur.

The microorganism of this invention elongates colourless aerial mycelia from branched substrate mycelia. Spore chains are formed in spirals on top of aerial mycelia. The spirals are open. Short spore chains representative of Section RA are also common. Neither whirl or ascospores are observed. Mature spore chains contain 10–20 spores per chain. The cultural characteristics of the microorganism on various agar media are described hereinbelow:

1. Yeast extract: malt extract agar
Growth: good, wrinkled, dry
Aerial mycelium: scant, powdery, light grey
Reverse: yellowish white
Soluble pigment: none 2. Oatmeal agar
Growth: good, flat, dry
Aerial mycelium: moderate, powdery, white
Reverse: pale yellow
Soluble pigment: none 3. Inorganic salts: starch agar
Growth: good, raised, dry
Aerial mycelium: good, powdery, grey
Reverse: grey-olive
Soluble pigment: none 4. Glycerol: asparagine agar
Growth: good, wrinkled, dry
Aerial mycelium: weak, powdery, white
Reverse: pale yellow
Soluble pigment: none 5. Peptone: yeast extract—iron agar
Growth: moderate, flat, sand-like
Aerial mycelium: none
Reverse: pale brown
Soluble pigment: none 6. Tyrosine agar
Growth: good, wrinkled, dry
Aerial mycelium: none
Reverse: light yellow
Soluble pigment: none 7. Sucrose: nitrate agar
Growth: good, wrinkled, sand-like
Aerial mycelium: scant, powdery, whitish
Reverse: pale yellow
Soluble pigment: none 8. Glucose: asparagine agar
Growth: good, wrinkled, dry
Aerial mycelium: weak, powdery, light grey
Reverse: pale yellow
Soluble pigment: none The optimum growth temperature range for the microorganism of this invention is from 25° C. to 37° C. This microorganism liquefies gelatin in glucose-peptone-gelatine medium, hydrolyzes starch in starch-inorganic salts agar, coagulates skimmed milk, does not form $H_2S$, and does not reduce nitrate. Str. sp. Y-86,36923 grows well on Czapek's solution agar.

No production of melanoid pigment is observed in tyrosine agar, peptone-yeast extract—iron agar or tryptone—yeast extract broth.

The carbon source assimilation pattern of this microorganism is as follows (in Pridham-Gottlieb's medium):
Positive: D-glucose, L-arabinose, D-xylose, m-inositol, D-mannitol, D-fructose, galactose, maltose, cellobiose, Na-glutamate, mannose, lactose, sucrose.
Weak: Rhamnose, raffinose.
Negative: Cellulose.

Str. sp. Y-86,36923 is inhibited by streptomycin at concentrations greater than 6.25 µg/ml, can tolerate NaCl at concentrations greater than 6% but less than 7%, and has a pH tolerance range of 6.0–9.0.

Str. sp. Y-86,36923 differs substantially from the known microorganisms which produce Cineromycin B and the related compound Albocycline. These are *Streptomyces cinerochromoges, Streptomyces brunneogriseus, Streptomyces roseocinereus,* and *Streptomyces roseochromogenes var albocyclini.*

The published information on the cultural and physiological characteristics of other known microorganisms show clear difference when compared with the microorganism of this invention.

In addition, when Str. sp. Y-86,36923 is fermented it produces the novel antibiotic Butalactin, in addition to the known antibiotic Cineromycin B.

From the above observations it is evident that the microorganism of this invention is a new species of Streptomyces.

It may be well understood to those skilled in the art that this invention is not limited to the particular organism which has been specified above but includes all those spontaneous and artificial mutants and variants derived from the said microorganism which are capable of producing the new antibiotic Butalactin.

A further subject of the present invention is a process for the production of Butalactin, said process comprising cultivating Str. sp. Y-86,36923 by fermentation at a pH between 6.0 and 9.0, preferably between 6 and 7, and a temperature between 18° and 40° C., preferably between 20° and 37° C., under aerobic conditions in a nutrient medium containing sources of carbon and nitrogen, nutrient inorganic salts, and trace elements, and isolating the compound from the culture broth in a known manner such as herein described.

The carbon sources used in the nutrient medium for production of the novel antibiotics may, for example, be glucose, starch, dextrin, glycerol, sucrose, molasses or oil. Sources of nitrogen used in the nutrient medium for production of the novel antibiotics may, for example, be soyabean meal, yeast extract, beef extract, malt extract, cornsteep liquor, peptone, gelatin or casein. Nutrient inorganic salts/mineral salts used in the nutrient medium for production of the novel antibiotics may, for example, be sodium chloride, magnesium sulfate, ammonium sulfate or calcium carbonate. As trace elements, for example, iron, manganese, copper, zinc or cobalt may be used.

Preferably Str. sp. Y-86,36923 is cultivated at about 27° C. (±1° C.) and pH about 7.0. The fermentation is preferably stopped after 23 to 48 hours when maximum yields of the compounds are obtained. The fermentation may, preferably, be a submerged fermentation. The process of fermentation and formation of Butalactin can be monitored by the antibacterial activity of the culture fluid and mycelium against *Staphylococcus aureus* 209 P and against *Escherichia coli* 9632 in agar medium, and by thin layer chromatography on silica gel plates with ethyl acetate as developing solvent.

If desired, an antifoaming agent such as Desmophen ® (Polyols, Bayer AG, Leverkusen, Germany) may be used in the nutrient medium during fermentation of the culture.

Butalactin can be obtained from the culture broth by extraction, preferably with a water-immiscible solvent after the pH has been adjusted to 6.5 to 7.5. The solvents could be ethyl acetate or chloroform; preferably it is ethyl acetate and the preferred pH is about 7.0. The solvent extract is concentrated to remove the solvent and then chromatographed further. Butalactin can also be obtained from the culture broth by direct adsorption on suitable absorbents such as Amberlite ® XAD-4 or 7 (Porous adsorbent resin based on polystyrene or acrylic acid ester, Rohm and Haas Co., U.S.A.), or Diaion ® HP-20 (high porosity adsorbent resin based on a polystyrenedivinylbenzene copolymer, Mitsubishi Chemical Industries, Japan); the preferred adsorbent being Diaion ® HP-20. The compound according to the invention is eluted from the adsorbent using appropriate mobile phases, such as chloroform, methanol or acetone, either singly, in combination with each other, or with water, and the eluates are then evaporated to dryness. The preferred eluant is methanol. The active eluates thus obtained are pooled and concentrated.

The aforementioned concentrated eluates or extracts containing Butalactin, can be further purified in a number of ways. For example, re-adsorption and elution processes with activated carbon, Amberlite ® XAD-4 and 7, Diaion ® HP-20, gel filtration with Sephadex ® LH-20 gel (gel of defined porosity on agarose, Pharmacia Fine Chemicals AB, Sweden) and its equivalents; adsorption chromatography on alumina and silica gel, can be conveniently combined for further purification. In addition, thin-layer chromatography, medium-pressure and high-pressure liquid chromatography using suitable adsorbents such as silica gel and modified silica gel-$C_{18}$ with suitable solvent systems may be used. Furthermore, counter current chromatography with a particular solvent system may work well for the said purpose. Preferably, repeated silica gel chromatography with ethyl acetate and petroleum ether (40° to 60° C.) as the eluting solvents is used. During this chromatography the known compound Cineromycin B is also separated out.

Butalactin is a pale yellow, thick syrup at room temperature (25° C.). It is soluble in water, methanol, ethanol, propylene glycol, dimethylsulfoxide, methylene chloride, ethyl acetate and chloroform. It is insoluble in hexane and petroleum ether (40° to 60° C.).

In the thin layer chromatography (TLC) systems indicated below Butalactin has the following values:
TLC plate: Precoated silica gel plate: Article No. 5544 from E. Merck, Darmstadt.

| Rf of | EtOAc |
|---|---|
| Butalactin | 0.44 |
| Cineromycin B | 0.51 |

BRIEF DESCRIPTION OF DRAWINGS

The analytical high-pressure liquid chromatography (HPLC) is shown in FIG. 1. HPLC was carried out using the following:

Column packing: ODS-Hypersil ®-10 μ, 4×(30+100) mm (Column material based on octadecyl silan, Shandon Labortechnik, Frankfurt/Main, Germany)

Flow Rate: 0.5 ml/min

Detection: 240 nm

Solvent: MeOH: Water (1:3)

Figure 1:
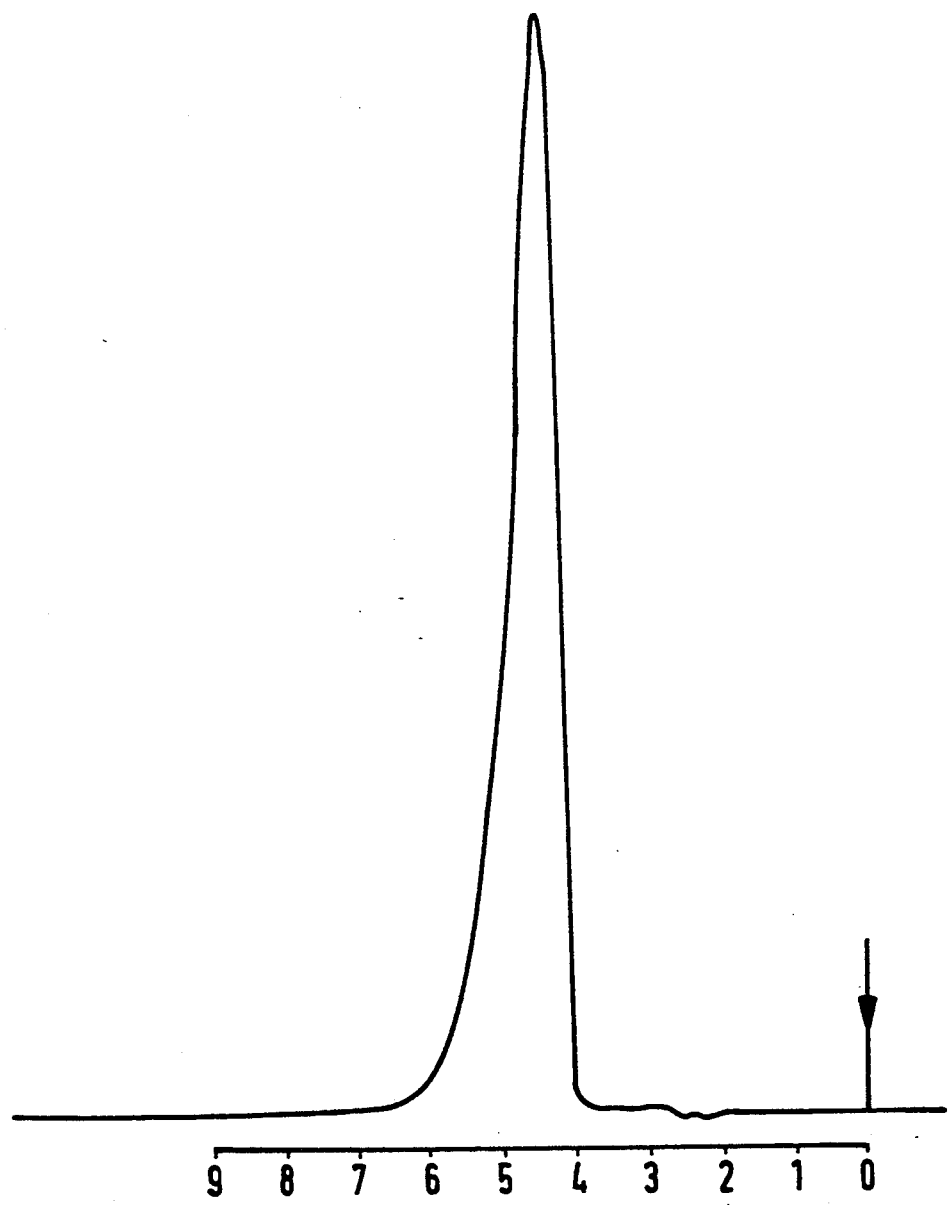
Figure 2:
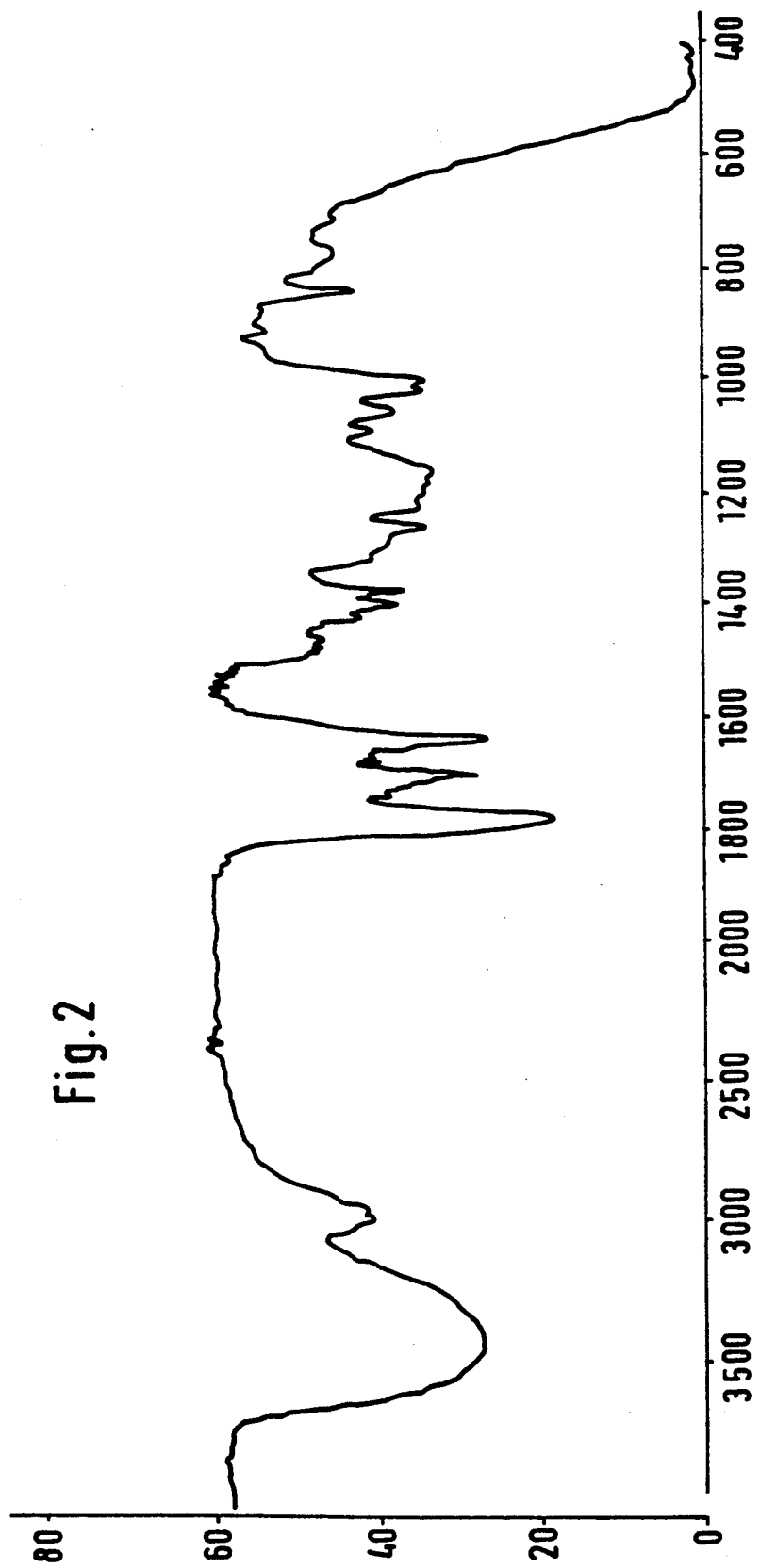
Figure 3:
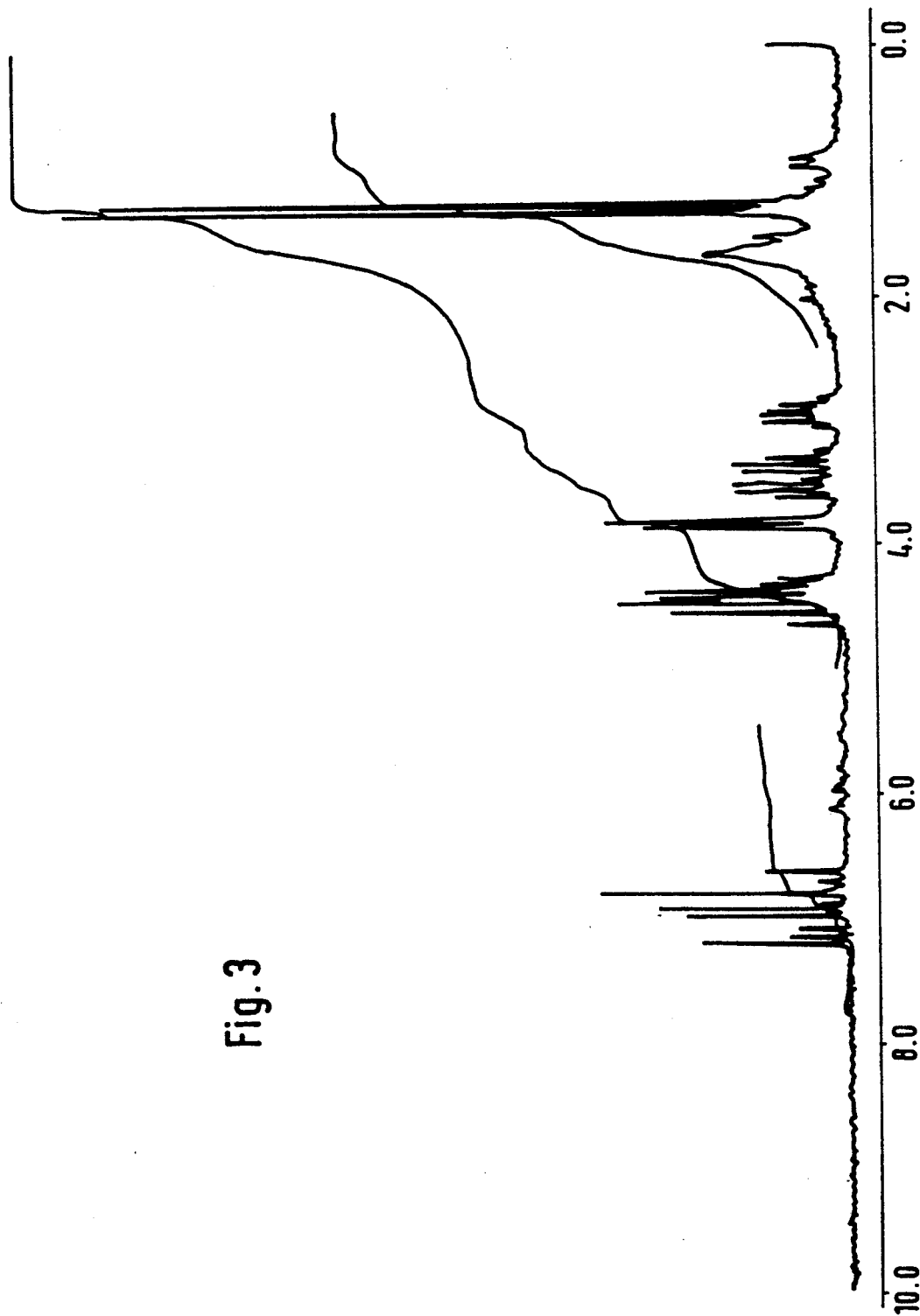
Figure 4:
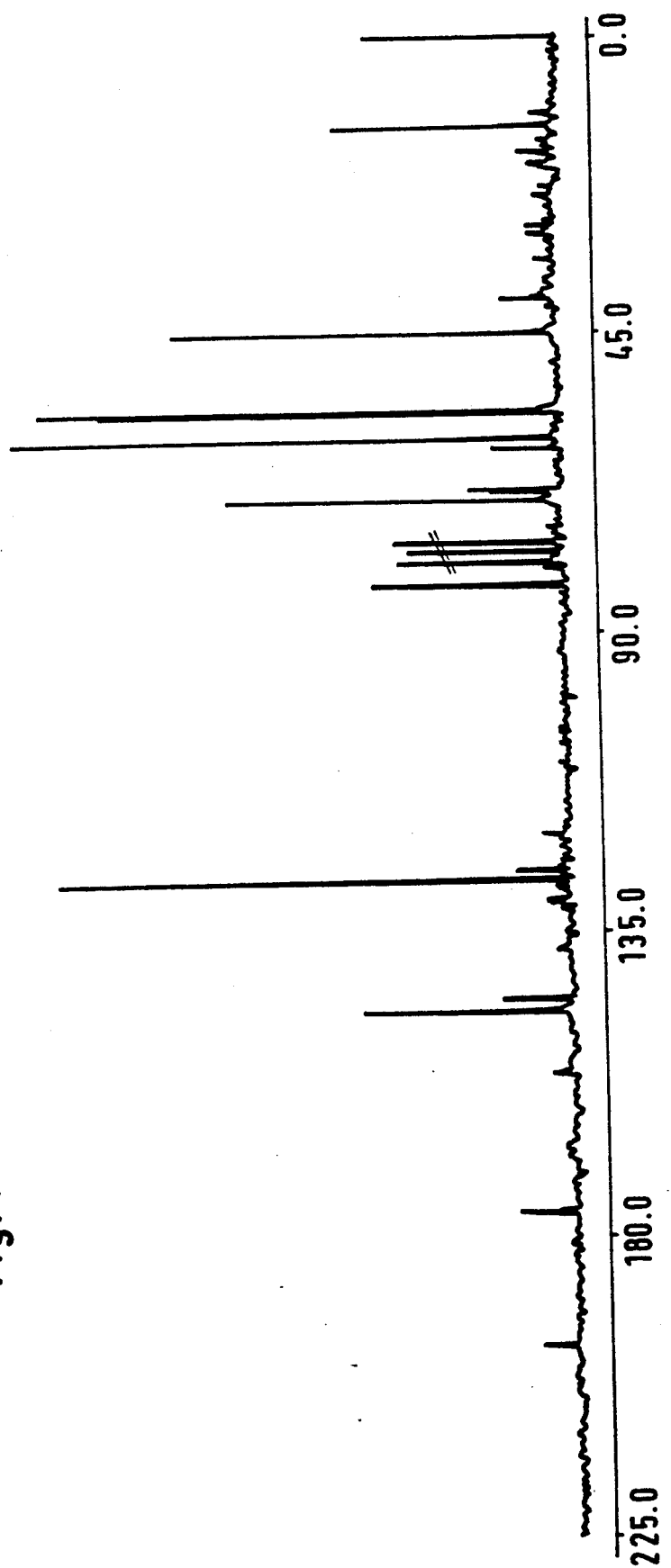

The spectroscopic data of Butalactin is listed below:

1. UV max in methanol and in 0.1 N HCl-methanol is 242 nm, in 0.1 N NaOH-methanol it shifts to 206 nm. The absorption spectrum was measured in the range of 200 to 800 nm using a Uvikon 810 Spectrophotometer.
2. The IR spectrum (neat) was determined using a Perkin Elmer P.E. 521 IR Spectrometer—see FIG. 2.
3. The $^1$H-NMR spectrum was determined on a 90 MHz JEOL FX-90Q instrument using CDCl$_3$ as solvent—see FIG. 3.
4. The $^{13}$C-NMR spectrum was determined on a 90 MHz JEOL FX-90Q instrument using CDCl$_3$ as solvent—see FIG. 4 of the accompanying drawings.
5. Mass Spectroscopy was carried out on a VG ZAB 3F instrument using Electron Impact (EI), Chemical Ionization (CI), and Fast Atom Bombardment (FAB) modes of ionization. The Molecular weight was found to be 242.0857 which corresponds to a Molecular formula of $C_{11}H_{14}O_6$.

The above data together with the chemical analysis indicates that Butalactin has a structure as shown in formula I.

Butalactin is active against gram-positive and gram-negative bacteria. When tested by the agar well method in Antibiotic Assay medium it has an activity which is shown in Table I below:

TABLE I

| Test Organism | Concentration | |
|---|---|---|
| | 2 mg/ml * | 1 mg/ml * |
| 1. Staphylococcus aureus 209 P | 21 | 19 |
| 2. Staphylococcus epidermidis 823 | 16 | 14 |
| 3. Staphylococcus haemolyticus 809 | 16 | 13 |
| 4. Streptococcus faecalis 21777 | 17 | 15 |
| 5. Streptococcus faecalis Eder | 23 | 21 |
| 6. Escherichia coli 9632 | 21 | 16 |
| 7. Enterobacter cloacae | 14 | 13 |
| 8. Citrobacter freundii | 17 | 15 |
| 9. Citrobacter 2046 E | 16 | 14 |
| 10. Proteus vulgaris | 15/21 | 12/20 |
| 11. Proteus mirabilis | 18 | 16 |
| 12. Pseudomonas aeruginosa | — | — |
| 13. Candida albicans | — | — |
| 14. Aspergillus niger | — | — |

* zone of inhibition in mm

In addition to the antibacterial activity Butalactin was also found to inhibit the biosynthesis of secondary metabolites, such as antibiotics, at concentrations that do not inhibit growth of the producing organism.

The invention will be further illustrated by preferred examples, but should not be considered as limited by those examples.

EXAMPLE I

Isolation of Streptomyces sp. Y-86,36923 from soil (a) Preparation of nutrient isolation media

| Medium 1: | Glucose | 1.0 g |
|---|---|---|
| | Glycerol | 1.0 g |
| | L-arginine | 0.3 g |
| | K$_2$HPO$_4$ | 0.3 g |
| | MgSO$_4$ × 7H$_2$O | 0.2 g |
| | NaCl | 0.3 g |
| | Yeast extract | 2.0 g |
| | FeSO$_4$ × 7H$_2$O | 10.0 mg |
| | CuSO$_4$ × 5H$_2$O | 1.0 mg |
| | ZnSO$_4$ × 7H$_2$O | 1.0 mg |
| | MnSO$_4$ × 7H$_2$O | 1.0 mg |
| | Agar | 15.0 g |
| | Distilled water | 1 liter |
| | pH | 6.5 |
| Medium 2: | Glucose | 2.0 g |
| | L-asparagine | 1.0 g |
| | K$_2$HPO$_4$ | 0.5 g |
| | MgSO$_4$ × 7H$_2$O | 0.5 g |
| | Soil Extract | 200 ml |
| | Agar | 15.0 g |
| | Distilled water | 800 ml |
| | pH | 8.0 |
| Medium 3: | Starch | 10.0 g |
| | Casein | 0.3 g |
| | KNO$_3$ | 2.0 g |
| | NaCl | 2.0 g |
| | K$_2$HPO$_4$ | 2.0 g |
| | MgSO$_3$ × 7H$_2$O | 0.05 g |
| | CaCO$_3$ | 0.02 g |
| | FeSO$_4$ × 7H$_2$O | 0.01 g |
| | Agar | 15.0 g |
| | Distilled water | 1 liter |
| | pH | 7.2-7.5 |

The media were sterilised at 121° C. for 30 minutes. In allcases, the sterilized media were cooled to 45° C., poured into petri plates and allowed to solidify.

(b) Preparation of soil suspension

One gram of soil was heated in a hot air oven to 110° C. for one hour. After cooling it was suspended in distilled water and shaken well. The soil was allowed to settle and the supernatent fluid was used to inoculate each one of the above mentioned media at a time.

(c) Inoculation of the isolation medium

One ml of the soil suspension was inoculated onto petri dishes containing 50 ml of any of the above mentioned nutrient isolation media.

(d) Isolation of Streptomyces sp. Y-86,36923

The inoculated petri dish was incubated at 37° C. for 10 days and Streptomyces sp. Y-86,36923 isolated from among the growing microorganisms.

EXAMPLE II

Cultivation of Streptomyces sp. Y-86,36923 for the fermantative production of Butalactin Streptomyces sp. Y-86,36923 was maintained on yeast extract-malt extract having the following composition:

| Malt extract | 10.0 g |
|---|---|
| Yeast extract | 4.0 g |
| Glucose | 4.0 g |
| Agar | 15.0 g |
| Distilled Water | 1 liter |
| pH | 7.0 |

The medium was distributed in test tubes and sterilized at 121° C. for 30 minutes. The tubes were cooled in a slanting position for preparation of agar slants. The slants were inoculated with the culture and incubated at 28° C. for 10 to 15 days when good growth and sporulation were observed. A suspension of the spores in distilled water from one slant was used to inoculate five 500 ml Erlenmeyer flasks each containing 100 ml of the seed culture medium.

Composition of the seed culture medium

| | |
|---|---|
| Glucose | 15.0 g |
| Soyabean meal | 15.0 g |
| Cornsteep liquor | 5.0 g |
| $CaCO_3$ | 2.0 g |
| NaCl | 5.0 g |
| Distilled water | 1 liter |
| pH | 6.5 |

The above medium was distributed in 100 ml amounts in 500 ml Erlenmeyer flasks and sterilized at 121° C. for 30 minutes. The flasks were cooled, inoculated with spore suspension or mycelial plugs and shaken at 240 r.p.m. for 72 hours at 27° C. (±1° C.) on a rotary shaker with 1.5 inch throw. The resultant growth was used to inoculate two hundred 500 ml flasks each containing 100 ml of the production culture medium at 2 to 4% (v/v).

Composition of the production medium

| | |
|---|---|
| Glucose | 10.0 g |
| Soluble starch | 10.0 g |
| Malt extract | 7.5 g |
| Peptone | 7.5 g |
| $MgSO_4 \times 7H_2O$ | 1.0 g |
| NaCl | 3.0 g |
| $CuSO_4 \times 5H_2O$ | 7.0 mg |
| $FeSO_4 \times 7H_2O$ | 1.0 mg |
| $MnCl_2 \times 4H_2O$ | 8.0 mg |
| $ZnSO_4 \times 7H_2O$ | 2.0 mg |
| Distilled water | 1 liter |
| pH | 6.5 |

The fermentation was carried out at 27° C. (±1° C.) on a rotary shaker at 240 r.p.m. with a 1.5 inch throw. When fermentation was discontinued at the end of 45 to 48 hours, the diameter of the zone of inhibition versus *Staphyloccus aureus* 209 P was 16 mm and versus *Escherichia coli as* 13 mm, when the culture filtrate was tested by the agar well (6 mm diameter) method and the pH of the culture fluid ranged from 6.8 to 7.0. The packed cell volume was 20% (v/v). The harvested culture broth containing the antibiotic was centrifuged to separate the mycelium and the culture fluid and further processed as described in Example IV.

EXAMPLE III

Cultivation of Streptomyces sp. Y-86,36923 for the fermentative production of Butalactin The procedure of Example II was repeated with the following differences:

Str sp. Y-86,36923 was grown on an agar medium with the following composition:

| | |
|---|---|
| Soluble starch | 10.0 g |
| $K_2HPO_4$ | 1.0 g |
| $MgSO_4 \times 7H_2O$ | 1.0 g |
| NaCl | 1.0 g |
| $(NH_4)_2SO_4$ | 2.0 g |
| $CaCO_3$ | 2.0 g |
| $FeSO_4 \times 7H_2O$ | 0.1 mg |
| $MnCl_2 \times 4H_2O$ | 0.1 mg |
| $ZnSO_4 \times 7H_2O$ | 0.1 mg |
| Agar | 15.0 g |
| Distilled water | 1 liter |
| pH | 7.2 |

The composition of the seed culture medium is similar to that in Example II.

Composition of production medium

| | |
|---|---|
| Glucose | 20.0 g |
| Peptone | 5.0 g |
| Beef extract | 5.0 g |
| $CaCO_3$ | 3.0 g |
| Distilled water | 1 liter |
| pH | 7.0 |

2 ml of Desmophen ® was added as antifoam agent. 10 l of the above medium were taken in a 15 l fermenter. The medium was sterilized trough direct and indirect steam for 20 minutes at 121° C. The fermenter was cooled and inoculated with seed culture (9% v/v). The fermentation was carried out at 27° C. (±1° C.) under stirred conditions at 120 r.p.m. with aeration at a rate of 60 to 70 liters per minute. When fermentation was discontinued at the end of 23 to 27 hours the pH of the culture broth was pH 7.4 and the diameter of the zone of inhibition versus *Staphylococcus aureus* 209 P was 22 mm and versus *Escherichia coli* was 14 mm when the culture filtrate was tested by the agar well method (6 mm diameter). The packed cell colume was 15% (v/v). The culture broth was processed as in Example V.

EXAMPLE IV

Isolation and purification of Butalactin

Approximately 16 liters of the culture filtrate, as obtained from Example II, was extracted twice with 10 liters each of ethyl acetate after adjusting the pH to 7.0. The aqueous layers were discarded and the combined ethyl acetate extracts where evaporated under vacuum to dryness. Approximately 6.4 g of crude extract was obtained. This crude extract was dry-charged onto a 5×20 cm silica gel (230–400 mesh size) column and eluted starting with a Petroleum ether (40°–60° C.) ethyl acetate mixture (1:1) followed by a stepwise (10%) increase in the ethyl acetate concentration to 100%. This procedure yielded 1.7 g of Fraction A, which eluted out at when the petroleum ether-ethylacetate gradient was 1:1, and 3.2 g of Fraction B which eluted out when the petroleum ether-ethylacetate gradient was 3:7. Fraction A was further purified by charging it into a 5×25 cm silica gel (230–400 mesh size) column followed by elution with a $CHCl_3$-EtOAc (1:1) to (3:7) gradient. The active fractions which were obtained with a $CHCl_3$-EtOAc (8:2) concentration were concentrated and chromatographed on a 2.4×90 cm Sephadex ® LH 20 column in methanol to yield 400 mg of antibiotic compound. This was further chromatographed on a 3×35 cm MPLC silica gel (30 µ) column and eluted at a flow rate of 10 ml/min with a chloroform to 2% methanol in chloroform stepwise (0.5%) gradient. When the methanol concentration was between 1–1.5% the active compound was eluted out and concentrated to yield 150 mg of a pure compound which was identified as the known antibiotic Cineromycin B.

Fraction B was charged, in 3 equal lots, onto 4.5×45 cm MPLC silica gel (30 µ) columns which were eluted with a petroleum ether-ethylacetate (5:5) to (3:7) gradient. The flow rate was maintained at 15 ml/min and the elution was monitored through a Knauer UV detector at 240 nm. Butalactin elutes out with a (4:6) petroleum ether-ethylacetate mixture. The active fractions were concentrated under vacuum to give 650 mg pure compound.

EXAMPLE V

Isolation and purification of Butalactin

Culture filtrates from two fermentor batches, as outlined in Example III, were pooled to give a volume of 17 liters. This was passed through a column containing 1 liter of Diaion ® HP-20; the column was washed with 10 liters of demineralized water and eluted with 5 liters of methanol. The active methanol eluates were concentrated in vacuo to dryness to give 8.8 g crude product. This was charged onto two 5×25 cm silica gel (230-400 mesh) columns, eluted with a chloroform-ethyl acetate (9:1) to (3:7) gradient to give two active fractions— Fraction A (2.3 g), containing Cineromycin B, which eluted out with chloroformethylacetate (8:2); and Fraction B (4.3 g), containing Butalactin, which eluted out when the chloroformethylacetate ratio was 5:5. Fraction B was purified in two lots by repeated chromatography on 5×60 cm silica gel (30 μ) MPLC colums with a petroleum ether-ethyl acetate (5:5) to (3:7) gradient. The flow rate was maintained at 20 ml/min and monitoring of elution was done with a Knauer UV detector at 240 nm. Concentration of the active eluates, which eluted out when the petroleum ether-ethyl acetate ratio was 4:6, yielded 550 mg pure compound.

We claim:

1. Butalactin, a compound of the formula I

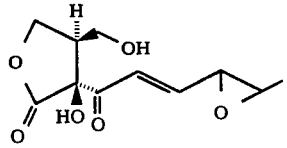

2. An antibiotic pharmaceutical composition comprising an antibiotically effective amount of the compound according to claim 1 together with a pharmaceutically acceptable carrier.

3. A method of controlling bacterial activity comprising administering to a host in need of such treatment an effective amount of the compound according to claim 1 together with a pharmaceutically acceptable carrier.

* * * * *